United States Patent [19]

Roehl et al.

[11] Patent Number: 5,166,060
[45] Date of Patent: Nov. 24, 1992

[54] PROCESS FOR THE PREPARATION OF PYRIDINE-2,3-DICARBOXYLIC ACIDS

[75] Inventors: Randall A. Roehl; George W. Matcham, both of Bridgewater; David I. Stirling, Fanwood, all of N.J.

[73] Assignee: Celgene Corporation, Warren, N.J.

[21] Appl. No.: 332,339

[22] Filed: Mar. 31, 1989

[51] Int. Cl.$^5$ .................. C12P 7/10; C12P 17/12; C12N 1/20; C12N 9/02

[52] U.S. Cl. .................. 435/122; 435/121; 435/877; 435/189

[58] Field of Search .............. 435/877, 859, 874, 122, 435/121, 189

[56] References Cited

U.S. PATENT DOCUMENTS 4,535,059  8/1985  Hsieh et al. .................. 435/877
4,654,303  3/1987  Hagedorn .................... 435/877

OTHER PUBLICATIONS

Eaton et al, "Metabolism of Dibutylphthalate . . . " *J. of Bacteriology* Jul. 1982, pp. 48–57.

Ribbons et al. *Arch Biochem Biophys*, 1970, vol. 138, pp. 557–565.
DeFrank et al., *J. Bacteriol.* vol. 129, pp. 1365–1374, 1977.
Kieslich, K., "Microbial Transformations", 1976, pp. 92–93.
Andreoni et al., *Biochem 5*, 1981, vol. 194, pp. 607–610.
Fersht, A., "Enzyme Structure and Mechanism", 1984, pp. 311–354, Freeman.

*Primary Examiner*—Irene Marx
*Attorney, Agent, or Firm*—Mathews, Woodbridge & Collins

[57] ABSTRACT

Pyridine-2,3-dicarboxylic acids are prepared by the action of 2,3-dihydroxybenzoate-3,4-dioxygenase on 2,3-dihydroxybenzoic acids in a liquid medium which lacks active decarboxylase and which has a pH from 4 to 9, an ionic strength below about 1 molar, and a low concentration of metal cations and complex anions. In close temporal proximity, the 2-hydroxy-3-carboxymuconic acid semialdehyde which forms is allowed to react with a source of ammonia or a primary amine, avoiding substantial decarboxylation.

13 Claims, No Drawings

PROCESS FOR THE PREPARATION OF PYRIDINE-2,3-DICARBOXYLIC ACIDS

The present invention pertains to a process for the preparation of pyridine-2,3-dicarboxylic acids.

BACKGROUND OF THE INVENTION

Pyridine dicarboxylic acids are useful chemical intermediates for the preparation of a wide variety of final compounds. For example, U.S. Pat. No. 4,518,780 describes cyclization of 2-carbamoyl-3-carboxypyridines, (obtained from pyridine-2,3-dicarboxylic acids) to yield imidazoline herbicides. A variety of such herbicides are known; see for example U.S. Pat. Nos. 4,188,487, 4,404,012, 4,459,408, 4,459,409, 4,638,068, 4,474,962, 4,562,257, 4,608,079, and 4,647,301, among others.

In addition to the traditional sources of pyridine derivatives, biological conversion of aromatic hydrocarbons such as toluene to 2-hydroxymuconic semialdehydes via catechol intermediates has been reported. Upon reaction with ammonia, the 2-hydroxymuconic semialdehydes yield picolinic acid (pyridine-2-carboxylic acid) derivatives. See U.S. Pat. Nos. 4,617,156, 4,654,303, 4,666,841, and 4,673,646.

While various optionally substituted hydrocarbons can be employed as substrates in these processes, they will not afford pyridine-2,3-dicarboxylic acids. Thus with benzoic acid (including that formed by oxidation of toluene), the initially operative enzymes are benzoate 1,2-dioxygenase and 1,2-dihydro-1,2-dihydroxybenzoate dehydrogenase, leading to conversion of the aromatic substrate to a catechol (see U.S. Pat. No. 4,654,303). The catechol in turn is converted to the hydroxymuconic acid semialdehyde derivative by the action of catechol 2,3-oxygenase. As described in the above references, however, the aromatic substrates, while optionally substituted in the meta and para positions, are unsubstituted in the position ortho to the carboxylic acid. In fact catechol 2,3-oxygenase is not operative on an aromatic compound having a carboxylic acid function adjacent to the catechol function, e.g., on a 2,3-dihydroxybenzoic acid type of structure.

Various workers have reported on the enzymatic degradation of 2,3-dihydroxybenzoic acid derivatives through the action of a different enzyme, namely 2,3-dihydroxybenzoate-3,4-dioxygenase (rather than a catechol-2,3-dioxygenase).

Ribbons et al., Arch. Biochem. Biophys., 1970, 138, 557–565, for example, noted formation of a semialdehyde product from a para-substituted 2,3-dihydroxybenzoic acid. Upon treatment with ammonia, however, this gave a picolinic acid product, not a dicarboxylic acid. In light of subsequent work, this would indicate decarboxylation had occurred.

DeFrank et al., J. Bacteriol., 1977, 129, 1365–1374, reported that a mutant of Pseudomonas putida PL-RF-1 which lacked decarboxylase converted 2,3-dihydroxycumate (2,3-dihydroxy-4-isopropylbenzoic acid) into a substance which absorbed at the 345 nm wavelength and which was postulated to be 2-hydroxy-3-carboxy-6-oxo-7-methylocta-2,4-dienoic acid. This decarboxylated spontaneously (or enzymatically in the presence of extracts from a wild-type strain producing active decarboxylate) to yield the isopropyl substituted 2-hydroxymuconic acid semialdehyde (2-hydroxy-6-oxo-7-methylocta-2,4-dienoic acid).

Andreoni et al., Biochem. J., 1981, 194, 607–610 also observed that when 2,3-dihydroxybenzoic acid was subjected to the action of a Pseudomonas putida extract, carbon dioxide was evolved with 2-hydroxymuconic acid semialdehyde being identified by NMR as the product.

Eaton et al., Arch. Microbiol., 1982, 132, 185–188, studied the action of several strains of Micrococcus on phthalate esters and noted in one case that 2,3-dihydroxybenzoate (presumably following meta oxidation to yield 3,4-dihydroxyphthalate and decarboxylation) also yielded 2-hydroxymuconic acid semialdehyde (absorbing at 375 nm). Since this most likely would occur through the action of a 2,3-dihydroxy-3,4-dioxygenase, Eaton et al. depicted 3-carboxy-2-hydroxymuconic acid semialdehyde as the putative cleavage product. Thus eventual formation of 2-hydroxymuconic acid semialdehyde could only be traced to decarboxylation as, they noted, in fact had been previously reported.

Engesser et al., Arch. Microbiol., 1988, 149, 198–206, noted the possibility of 2,3-dihydroxy-4-trifluoromethylbenzoic acid being oxidized to the corresponding 3-carboxy-2-hydroxymuconic acid semialdehyde (2-hydroxy-3-carboxy-6-oxo-7,7,7-trifluorohepta-2,4-dienoic acid). They too found, however, that decarboxylation occurred and that the intermediate in fact was the corresponding 2-hydroxymuconic acid semialdehyde 2-hydroxy-6-oxo-7,7,7-trifluorohepta-2,4-dienoic acid, not the 3-carboxy intermediate. Hence reaction of this intermediate with ammonium produced 6-trifluoromethylpicolinic acid with no evidence of 6-trifluoromethylpyridine-2,3-dicarboxylic acid having been formed.

Hence while the possibility of 3-carboxy-2-hydroxymuconic acid semialdehydes being formed from 2,3-dihydroxybenzoate structures under the influence of a 2,3-dihydroxy-3,4-dioxygenase has been postulated, there is at best only circumstantial evidence for its formation and in no case has conversion to pyridine dicarboxylic acids been observed. Quite to the contrary, in each case in which the semialdehyde product has been reacted with ammonia, a picolinic acid (a monocarboxylic acid) rather than a pyridine dicarboxylic acid has been formed.

DETAILED DESCRIPTION

The present invention is based on the discovery that 3-carboxy-2-hydroxymuconic acid semialdehyde can be formed from 2,3-dihydroxybenzoate structures under the influence of a 2,3-dihydroxybenzoate-3,4-dioxygenase but because the same is so susceptible to chemical and enzymatic decarboxylation, it normally cannot be further processed, as for example to a pyridine-2,3-dicarboxylic acid under the influence of ammonia, except under specified parameters.

The present invention thus provides a process for the preparation of pyridine dicarboxylic acids of the formula:

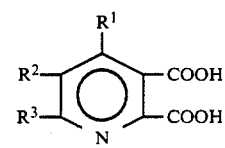

in which

R¹ is hydrogen, alkyl of 1 to 12 carbon atoms, alkoxy of 1 to 12 carbon atoms, halogeno, mercapto, phenyl, or phenoxy;

R², taken independently of R³, is hydrogen, alkyl of 1 to 12 carbon atoms, alkoxy of 1 to 12 carbon atoms, halogeno, mercapto, phenyl, or phenoxy;

R³, taken independently of R², is hydrogen or alkyl of 1 to 12 carbon atoms, unsubstituted or substituted with halogeno or alkoxy of 1 to 12 carbon atoms, or R² and R³, taken together, are the residue of an aromatic ring fused to the depicted pyridine ring, and the salts thereof.

According to the process of the present invention, a 2,3-dihydroxybenzoic acid of the formula:

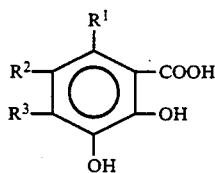

II.

in which R¹, R², and R³ are as defined above, or a salt thereof, is subjected to the action of 2,3-dihydroxybenzoate-3,4-dioxygenase in a liquid medium lacking active decarboxylase and having a pH from 4 to 9, an ionic strength below about 1 molar, and a low concentration of metal cations and complex anions, to accumulate 2-hydroxy-3-carboxymuconic acid semialdehyde, and in temporal proximity, reacting the 2-hydroxy-3-carboxymuconic acid semialdehyde thus formed with a source of ammonia or a primary amine.

Throughout this specification reference to the carboxylic acid function is intended to include the anionic form and the salts thereof, as for example the alkali metal, alkaline earth metal, ammonium, and amine salts.

The 2,3-dihydroxybenzoate-3,4-dioxygenases employed are metapyrocatechases which have been reported in the literature to be present in a variety of naturally occurring microorganisms such as Pseudomonas [see De Frank et al., supra] and Micrococci [see Eaton et al., supra]. In the metabolic pathways of these wild-type species, decarboxylating enzymes also will be present so that the 2-hydroxy-3-carboxymuconic acid semialdehyde produced is quickly converted to 2-hydroxymuconic acid semialdehyde. Moreover it has been found that 2-hydroxy-3-carboxymuconic acid semialdehyde itself is highly labile to chemical decarboxylation so that even if the enzymatic environment is free of active decarboxylase, loss of the 3-carboxy group occurs extremely rapidly if not virtually immediately. The present process therefore requires not only that the enzymatic environment be free of active decarboxylase but that the formation of 2-hydroxy-3-carboxymuconic acid semialdehyde and subsequent reaction with ammonia or a primary amine occur under conditions which minimize chemical decarboxylation.

Isolation of the enzyme 2,3-dihydroxybenzoate-3,4-dioxygenases free of active decarboxylase can be accomplished by cloning techniques or mutant selection from wild-type species. Mutant selection involves a three step procedure: (i) identification of strains which utilize dihydroxybenzoate as the sole carbon source; (ii) mutagenesis of the strains so isolated; and (iii) mutant selection for the ability to oxidize 2,3-dihydroxybenzoate but a deficiency in its ability to use 2,3-dihydroxybenzoate as a carbon source.

The first step of the procedure is performed by screening for growth on a minimal salt agar medium containing dihydroxybenzoate, or a precursor such as cumene, phthalate, benzoate, as the sole carbon source to select wild-type strains which utilize 2,3-dihydroxybenzoate as a carbon source.

In the second step of the procedure, the selected strain is subjected to the action of a physical, chemical, or biological mutagenic agent such as exposure to UV radiation, to chemical agents such as N-methyl-N'-nitroso-N-nitrosoguanidine or ethyl methanesulfonate, or biologically through the use of transposons. See in general, *Manual of Methods for General Bacteriology*, P. Gerhardt, Ed., American Soc. for Microbiol,, 1981, Chapter 13.

The third step of the procedure involves mutant enrichment by culturing the mutagenized strain in minimum medium in the presence of dihydroxybenzoate and one or more antibiotics which interfere with formation of normal cell wall structure, such as cycloserine, penicillin, carbenicillin, etc. to select for mutants which are deficient in their ability to use dihydroxybenzoate as a carbon source. Again these general procedures are well known. See *Manual of Methods for General Bacteriology*, supra.

Following incubation, viable cells are recovered and cultured on minimal salt agar containing pyruvate and dihydroxybenzoate. This procedure can be repeated several times, although mutants suitable for the present purpose generally are obtained in the first cycle. The desired mutants are readily identified since they are characterized by the production of yellow colored zones around or in the colonies, indicating the accumulation of muconic acid semialdehydes.

For reasons discussed below, minimal salts media are preferably utilized in all culturing procedures. A typical composition contains 0.6 g/L of disodium phosphate, 0.3 g/L of monopotassium phosphate, 0.5 g/L of sodium chloride, 0.1 g/L of ammonium chloride, 0.1 mmol/L of calcium chloride, and 1mmol/L of magnesium sulfate, in distilled water.

The enzyme actually used can be isolated from mutants of ubiquitous wild-type microorganisms as described above or expressed by other species such as *E. coli* which have been modified by recombinant techniques. Thus having selected a suitable source strain as discussed above in step 1, the 2,3-dihydroxybenzoate-3,4-dioxygenase gene can be cloned into another species free of decarboxylase for 2-hydroxy-3-carboxy-6-oxohexa-2,4-dienoic acid.

From analysis to date, it appears the 2,3-dihydroxybenzoate-3,4-dioxygenase gene is a 1.8 kb SalI fragment contained within a 6.2 kb EcoRI fragment. Enzyme produced by *E. coli* into which this fragment has introduced has been found to be particularly suitable for use in the process of the present invention since the relevant decarboxylase is not normally present in *E. coli*.

The actual enzymatic conversion can be effected either by conventional culturing techniques or by bringing the enzyme into contact with the substrates of Formula II. The enzyme can be free, in form of either a cell free extract or a whole cell preparation, or immobilized on a suitable support or matrix such as a cross-linked dextran or agarose, silica, polyamide, or cellulose, or encapsulated in polyacrylamide, alginates, or fibers. Methods for such immobilization are described in the literature (see, for example, *Methods of Enzymology*, 44. 1976).

In addition to the enzyme preparation being free of active decarboxylase, it is also important to conduct the transformation within certain parameters which minimize chemical decarboxylation. Decarboxylation can be monitored by simple UV absorbance measurements since at neutral pH, the desired 2-hydroxy-3-carboxy-6-oxo-hexa-2,4-dienoic acid has a strong absorbance peak at 340 nm whereas the decarboxylated 2-hydroxy-6-oxohexa-2,4-dienoic acid has a strong absorbance peak at 375 nm. Thus decarboxylation can be quantitatively followed by the disappearance of the peak at 340 nm and appearance of a peak at 375 nm.

Among the parameters affecting chemical decarboxylation are pH, ionic strength, concentration of metal cations and complex anions, and temperature. The pH should be maintained above about 4 and below about 9, preferably at from about 5 to about 7. At pH 4.4 and a temperature of 52° C., for example, the half-life of 2-hydroxy-3-carboxy-6-oxohexa-2,4-dienoic acid is about 2 minutes and at pH 8 it is about 1.5 minutes at the same temperature. At pH 6, on the other hand, the half-life increase about six fold, to about 13 minutes.

Moreover, it is desirable to maintain the ionic strength below about 1 molar since the lower the ionic strength, the greater the half-life. Also important is the concentration of metal cations and complex anions. For example, the presence of 1 mM of nickel will reduce the half-life by as much as 20%. Use of excessive amounts of buffer, leading to a high concentration of complex ions such as phosphate anions, also has a detrimental effect. Reducing the concentration of sodium phosphate for example from 100 mM to 15 mM produces a 4 to 5 fold increase in half-life. Finally, lower temperature significantly reduces chemical decarboxylation, a reduction of 15° C. for example increasing the half-life of 2-hydroxy-3-carboxy-6-oxohexa-2,4-dienoic acid more than four-fold. Desirably the temperature should be below about 50° C. Thus pH, ionic strength, the concentration of metal cations and complex anions, and temperature all have an effect on the rate of chemical decarboxylation. Of these factors, pH, the concentration of complex anions, and temperature appear to be particularly important. By proper selection, it is possible to decrease the rate of decarboxylation to the point at which substantial quantities of the particular 2-hydroxy-3-carboxy-6-oxohexa-2,4-dienoic acid accumulate and can be reacted with a source of ammonia or a primary amine for formation of the desired pyridine dicarboxylic acid. It is to be appreciated that the precise combination of these parameters will vary, depending upon the particular substrate employed, and that some experimentation to arrive at the preferred combination may be necessary. As noted, however, the objective is to minimize decarboxylation and arriving at the optimum conditions for any given embodiment can be readily ascertained with UV spectrophotometric analysis.

The reaction with a source of ammonia or a primary amine is performed in close temporal proximity to the formation of 2-hydroxy-3-carboxy-6-oxohexa-2,4-dienoic acid. As noted this can occur virtually simultaneously by conducting the enzymatic reaction in the presence of a source of ammonia or a primary amine, or by bringing the 2-hydroxy-3-carboxy-6-oxohexa-2,4-dienoic acid into contact with a source of ammonia or a primary amine shortly after formation. Conditions which discourage decarboxylation, as discussed above, should be maintained. Hence the product should not be exposed to excessive temperatures nor to a high concentration of complex anions. It similarly is desirable to avoid conditions during the early enzymatic processing which can contribute to decarboxylation. For example, excessive use of buffer can contribute to a high concentration of phosphate, leading to an increase in the rate of decarboxylation, as shown above. It is for this reason that minimal salts media should be employed in all culturing procedures.

Apart from the structural requirements in the 1-, 2-, and 3-positions of the aromatic ring, the starting material can carry a wide variety of substituents in the 5- and 6-positions ($R^2$ and $R^1$, respectively). In addition to hydrogen, each of $R^1$ and $R^2$, independently of the other, can be alkyl of 1 to 12 carbon atoms, alkoxy of to 12 carbon atoms, halogeno, mercapto, phenyl, or phenoxy. Alternatively, $R^1$ and $R^2$, taken together, are the residue of an aromatic ring fused to the depicted ring. Hence, utilizing 3,4-dihydroxynaphthalene-2-carboxylic acid, there is obtained quinoline-2,3-dicarboxylic acid.

The 4-position of the compounds of Formula II can be unsubstituted ($R^3$=hydrogen) or can be substituted with alkyl of 1 to 12 carbon atoms, which in turn can be unsubstituted or substituted with halogeno or alkoxy of 1 to 12 carbon atoms.

Representative starting materials are 2,3-dihydroxybenzoic acid, 2,3-dihydroxy-5-methylbenzoic acid, 2,3-dihydroxy-5-ethylbenzoic acid, 2,3-dihydroxy-5-bromomethylbenzoic acid, 2,3-dihydroxy-5-chloromethylbenzoic acid, 2,3-dihydroxy-5-dibromomethylbenzoic acid, 2,3-dihydroxy-5-dichloromethylbenzoic acid, 3,4-dihydroxy-2-carboxynaphthalene, 2,3-dihydroxy-5-methoxymethylbenzoic acid, 2,3-dihydroxy-5-ethoxymethylbenzoic acid, 2,3-dihydroxy-5-propoxymethylbenzoic acid, and 2,3-dihydroxy-5-isopropoxymethylbenzoic acid. These respectively yield pyridine-2,3-dicarboxylic acid, 5-methylpyridine-2,3-dicarboxylic acid, 5-ethylpyridine-2,3-dicarboxylic acid, 5-bromomethylpyridine-2,3-dicarboxylic acid, 5-chloromethylpyridine-2,3-dicarboxylic acid, 5-dibromomethylpyridine-2,3-dicarboxylic acid, 5-dichloromethylpyridine-2,3-dicarboxylic acid, quinoline-2,3-dicarboxylic acid, 5-methoxymethylpyridine-2,3-dicarboxylic acid, 5-ethoxymethylpyridine-2,3-dicarboxylic acid, 5-propoxymethylpyridine-2,3-dicarboxylic acid, and 5-isopropoxymethylpyridine-2,3-dicarboxylic acid. Use of a primary amine, notably an alkyl amine of 1 to 6 carbon atoms, in place of a source of ammonia leads to generation of the quaternary salt of the pyridine-2,3-dicarboxylic acid. In general it is desirable to add the ammonia in a less basic form. Thus as a source of ammonia, one can employ a salt with a weak, non-interfering acid, such ammonium acetate or ammonium sulfate.

The preferred starting materials by reason of the commercial value of the final pyridine dicarboxylic acids thus are those in which $R^1$ and $R^3$ are hydrogen and $R^2$ is hydrogen or alkyl of 1 to 6 carbon atoms, unsubstituted or substituted with halo or alkoxy of 1 to 6 carbon atom, particularly those compounds in which $R^2$ is hydrogen, methyl, or ethyl.

The 2,3-dihydroxybenzoic acids of Formula II can be added directly or generated from a suitable precursor such as a phthalic or benzoic acids. Particularly useful in this regard are benzoic acids of the formula:

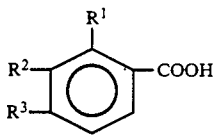

III.

in which $R^1$, $R^2$, and $R^3$ are as herein defined, by the action of a benzoate-2,3-oxygenase and benzoate-2,3-dihydro-2,3-dioldehydrogenase under enzymatically reactive conditions. Such formation can be accomplished concurrently with the subsequent transformation by utilizing benzoate-2,3-oxygenase, benzoate-2,3-dihydro-2,3-dioldehydrogenase, and 2,3-dihydroxybenzoate-3,4-dioxygenases. Alternatively, the transformations can be performed sequentially in discrete steps.

The process can be practiced by formation of the 2-hydroxy-3-carboxymuconic acid semialdehyde followed by in situ treatment with ammonium or a primary amine. Alternatively the enzymatic conversion of the 2,3-di-hydroxybenzoic acids of Formula II can be conducted in the presence of a source of ammonia, such as an ammonium salt, or of the primary amine. For example, the selected mutant can be cultured in minimal medium containing glucose and a 2,3-dihydroxybenzoic acid of Formula II, the cells then harvested, and the supernatant incubated with ammonium sulfate. Alternatively, the 2,3-dihydroxybenzoic acids of Formula II can be fed into a buffered solution of soluble cell extract containing the enzyme and ammonium sulfate to form the corresponding pyridine dicarboxylic acid directly. Similarly, a 2,3-dihydroxybenzoic acid of Formula II or a precursor therefor can be passed over the immobilized enzyme and the eluant subsequently brought into contact with a source of ammonia such as ammonium sulfate. Alternatively, a 2,3-dihydroxybenzoic acid of Formula II is passed over the immobilized enzyme in the presence of a source of ammonia such as ammonium sulfate or ammonium acetate.

The following examples will serve to further typify the nature of this invention but should not be construed as a limitation on the scope thereof, which is defined solely by the appended claims.

EXAMPLE 1

Isolation of Suitable Strains

Soil samples are used to inoculate minimal salts agar medium containing 5mM of 2,3-dihydroxybenzoic acid as the sole carbon source. Numerous isolates are thereby obtained. Typical are two Pseudomonas strains (labelled CEL 449 and CEL 3504) which are Gram negative rods producing a fluorescent pigment on King's B medium.

CEL 449 is mutagenized by centrifuging a 5ml sample of a culture (grown to exponential phase in LB broth), suspending the isolated cells in 5ml of 0.1M sodium citrate (pH 5.5) and 5 μg/ml of N-methyl-N'-nitroso-N-nitrosoguanidine for 30 minutes, and washing the cells.

Minimal salts medium containing 5mM of 2,3-dihydroxybenzoic acid, 1 mg/ml of carbenicillin, and 100μg/ml of D-cycloserine are inoculated with the washed cells and incubated for 15 hours. The cells are collected by centrifugation and washed with distilled water. Viable cells are recultured in minimal medium containing 10 mM of pyruvate. The mutagenesis/mutant enrichment steps can be repeated, although suitable mutants generally are obtained on the first cycle. The cell culture is spread onto minimal salts agar medium containing 1 mM of pyruvate and 5 mM of 2,3-dihydroxybenzoic acid. This is incubated at 30° C. and colonies which grow are transferred to minimal salts agar medium containing 1 mM of pyruvate and 5 mM of 2,3-dihydroxybenzoic acid and those colonies which produced a yellow color are selected for their inability to utilize 2,3-dihydroxybenzoic acid as a carbon source. One colony (over 60 such colonies can be identified) produced by the foregoing method was designated CEL 454.

A second strain, designated CEL 464, was produced by repeating the foregoing procedures but utilizing CEL 3504 as the source strain.

EXAMPLE 2

Production of Pyridine-2,3-dicarboxylic Acid Using Cell Extract

CEL 454 is cultured for 16 hours in 500 mL. of LB broth containing 30 mM of pyruvate. One millimolar dihydroxybenzoate is added and the culture is further incubated for 30° C. for two hours. The cells are washed, harvested by centrifugation, and lysed in a French press. Cell debris is removed by ultracentrifugation at 100,000×g at 4° C. for two hours to yield soluble cell extract which is stable for several months when stored at −85° C.

Two milliliters of soluble cell extract are added to 25 mL of 10 mM of sodium phosphate buffer (pH 7.0) and 10 mM of ammonium sulfate. Into this is fed a stock solution of 250 mM of sodium dihydroxybenzoate at a rate of approximately 1 mM/hour. After approximately 24 hours, the reaction is terminated (by addition of 100 μg/ml of proteinase K). Chromatographic analysis indicates 4.1 mM of pyridine-2,3-dicarboxylic acid, approximately 668 mg/L, had accumulated.

EXAMPLE 3

Production of Pyridine-2.3-dicarboxylic Acid Using Whole Cells

CEL 464 is grown in 1 L of minimal medium containing 20 mM of glucose for approximately 15 hours. One millimole of 2,3-dihydroxybenzoic acid is added and the culture incubated for 2 hours. The cells are harvested by centrifugation, concentrated 20-fold in 10 mM phosphate buffer, 10 mM of 2,3-dihydroxybenzoic acid, and 50 mM of ammonium sulfate, and incubated aerobically for six hours at 30° C. After removal of the cells by centrifugation, the supernatant contains 4.0 mM of pyridine-2,3-dicarboxylic acid.

Example 4

Cloning of 2,3-Dihydroxybenzoate-3,4-Dioxgenase Gene

CEL 3504 is cultured for 16 hours in 500 mL. of LB broth, harvested by centrifugation, and washed with M9 minimal salts solution {Miller, *Experiments in Molecular Genetics*, Cold Spring Harbor Laboratory, Cold Spring Harbor, N.Y., (1987)}. The cell pellets are suspended in 50 mM of Tris-HCl (pH 8.0) containing 25% sucrose to give a final volume of 8.0 mL, to which 5.0 mL of lysozyme (4 mg/mL in 0.25M sodium ethylenediaminetetraacetic acid at pH 8.0) are added. This mixture is incubated on ice for five minutes and 4.5 mL of 2% Triton X-100 in 50 mM of Tris-HCl (pH 8.0) and 60 mM of sodium ethylenediaminetetraacetic acid are added and mixed by inversion. After incubation for 16 hours at 4° C., cell debris was removed by centrifugation at 27,000×g at 4° C.

To the supernatant are added 6 mL of 5M sodium chloride solution and 7.5 mL of 40% of polyethylene glycol 4000 in 50 mM of Tris-HCl and 20 mM of sodium ethylenediaminetetraacetic acid and the whole mixed by inversion and incubated for 16 hours at 4° C. The DNA is pelleted by centrifugation at 3,000×g at 4° C., suspended in 10 mM Tris-HCl (pH 8.0) containing 1 mM of sodium ethylenediaminetetraacetic acid and 170 mM of sodium chloride, and purified by cesium chloride gradient centrifugation. The single chromosomal DNA band is pulled from the gradient tube, ethidium bromide is extracted with isopropanol saturated with cesium chloride, and the DNA dialysed in 10 mM Tris-HCl (pH 8.0) and 1 mM of sodium ethylenediaminetetraacetic acid.

Plasmid vector pUC19 (Norrander et al., Gene, 26, 101-106) from E. coli HB101 is purified using the procedure of Maniatis et al., Molecular Cloning: a Laboratory Manual, Cold Spring Harbor Laboratory, Cold Spring Harbor, N.Y., (1982). The purified CEL 3504 DNA and pUC19 DNA are digested with restriction enzyme EcoR and ligated with T4 DNA ligase. Competent cells of E. coli DH5α are transformed selecting ampicillin resistance on LB agar medium (Miller, supra) containing 100 μg/mL of ampicillin, 0.1 mM of isopropylthio-β-D-galactoside, and 250 μg/mL of 5-bromo-4-chloro-3-indolyl-β-D-galactoside.

White colonies unable to express β-galactosidase are patched to M9 minimal salts agar containing 100 μg/mL of ampicillin, 0.1 mM of isopropylthio-β-D-galactoside, and 1 μg/mL of thiamine. The plates are incubated for 48 hours at 37° C. and then sprayed with a solution of 0.25M 2,3-dihydroxybenzoate. Patches of cell growth producing a yellow zone are restreaked onto LB agar containing ampicillin to yield the desired recombinant E. coli strain.

Plasmid DNA isolated from such selected strains (pCE41 isolated from CEL 194) is purified by cesium chloride gradient centrifugation and analyzed by restriction enzyme digestion. A 6.2 kb EcoRI fragment carries the 2,3-dihydroxybenzoate-3,4-dioxgenase gene.

EXAMPLE 5

Expression 2,3-dihydroxybenzoate-3,4-dioxgenase and Half-life Analysis

CEL 194(pCE41) is grown aerobically at 37° C. on a liquid medium containing 10 g/L of bactotryptone, 5 g/L of yeast extract, 10 g/L of sodium chloride, 0.1 mg/L of ampicillin, and 0.1 mmol/L of isopropylthio-β-D-galactoside. Cells are harvested by centrifugation at the end of exponential growth, resuspended in 10 mL of 10 mM sodium phosphate buffer (pH 6.8), and incubated aerobically at 37° C.

2,3-Dihydroxybenzoate (0.1 mM) then is added. Within twenty minutes, UV spectrophotometry indicates a strong band at 340 nm with no band at 375 nm, indicating the formation of 2-hydroxy-3-carboxymuconic acid semialdehyde with no decarboxylation. Removal of cells by centrifugation provides a solution of 2-hydroxy-3-carboxymuconic acid semialdehyde in 10 mM phosphate buffer. The following table exemplifies the effect of various parameters on the half-life of 2-hydroxy-3-carboxymuconic acid semialdehyde, decarboxylation being monitored by the disappearance of the 340 nm absorbance and the appearance of the 375 nm absorbance. In each case, the variable is underlined.

TABLE I

| pH | Ionic Strength | Anion conc. | Metal | Temp. | Half-life |
|---|---|---|---|---|---|
| 4.4 | .5M | 100 mM[1] | No | 52° C. | 2 min |
| 6.0 | 0.5M | 100 mM[1] | No | 52° | 13 min |
| 8.0 | 0.5M | 100 mM[2] | No | 52° | 1.5 min |
| 7.0 | 0.5M | 100 mM[3] | No | 52° | 4.5 min |
| 7.0 | 0.385M | 100 mM[3] | No | 52° | 5.5 min |
| 7.0 | 0.27M | 100 mM[3] | No | 52° | 7.3 min |
| 6.5 | 0.5M | 100 mM[3] | No | 52° | 5 min |
| 6.5 | 0.5M | 60 mM[3] | No | 52° | 11.5 min |
| 6.5 | 0.5M | 15 mM[3] | No | 52° | 23 min |
| 7.0 | 0.5M | 100 mM[3] | No | 37° | 14 min |
| 7.0 | 0.5M | 100 mM[3] | Yes[4] | 37° | 11 min |
| 6.0 | 0.5M | 10 mM[1] | No | 52° | 26 min |
| 6.0 | 0.5M | 10 mM[1] | No | 37° | 120 min |

Notes
[1] Sodium succinate
[2] Tris/HCl
[3] Sodium phosphate
[4] 1 mmol NiCl$_2$

EXAMPLE 6

Production of Pyridine-2,3-dicarboxylic Acid Using Cell Extract

CEL 194(pCE41) is cultured for 16 hours at 37° C. in 500 mL. of LB broth containing 100 μg/mL of ampicillin and 0.1 mM of isopropylthio-β-D-galactoside. The cells are harvested by centrifugation, washed, suspended in 10 mM of sodium phosphate buffer (pH 7.5), and lysed in a French press. Cell debris is removed by ultracentrifugation at 100,000×g at 4° C. for two hours to yield soluble cell extract.

Two milliliters of soluble cell extract are added to 18 mL of 10 mM of sodium phosphate buffer (pH 7.5), 10 mM of ammonium sulfate, and 0.5 mM of 2,3-dihydroxybenzoate in a 20 mL reactor. The mixture is incubated with stirring at 30° C. with additional 2,3-dihydroxybenzoate being added at a rate of approximately 10 μm/hour. After 16 hours, approximately 535 mg/L of pyridine-2,3-dicarboxylic acid accumulate.

EXAMPLE 7

Production of Pyridine-2,3-dicarboxylic Acid Using Whole Cells

CEL 194(PCE41) is cultured in 4 L of LB medium at 37° C. for 16 hours. The cells are harvested by centrifugation and used to inoculate 400 mL of 1 mM Trisacetate buffer containing 10 mM of ammonium acetate in a fermenter. The culture is incubated at 37° C. with aeration, maintaining a pH of 8.0 by addition of acetic acid or ammonium hydroxide as necessary. 2,3-Dihydroxybenzoic acid is introduced at a rate of 30 μmol/min. After 17 hours, pyridine-2,3-dicarboxylic acid has accumulated to a concentration of 418 mg/L.

The microorganisms referred to herein have been deposited with the the American Type Culture Collection, 12301 Parklawn Drive, Rockville, Md. as follows:

| CEL Designation | ATCC No. |
|---|---|
| CEL 449 | 53,886 |
| CEL 454 | 53,887 |

| CEL Designation | ATCC No. |
| --- | --- |
| CEL 464 | 53,888 |
| CEL 3504 | 53,889 |
| CEL 194 (pCE41) | 67,924 |

What is claimed is:

1. Process for the preparation of pyridine-2,3-dicarboxylic acid of the formula:

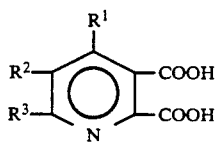

in which:

$R^1$ is hydrogen, alkyl of 1 to 12 carbon atoms, alkoxy of 1 to 12 carbon atoms, halogeno, mercapto, phenyl, or phenoxy;

$R^2$, taken independently of $R^3$, is hydrogen, alkyl of 1 to 12 carbon atoms, alkoxy of 1 to 12 carbon atoms, halogeno, mercapto, phenyl, or phenoxy; and $R^3$, taken independently of $R^2$, is hydrogen or alkyl of 1 to 12 carbon atoms, unsubstituted or substituted with halogeno or alkoxy of 1 to 12 carbon atoms, or $R^2$ and $R^3$, taken together, are the residue of an aromatic ring fused to the depicted pyridine ring which comprises subjecting a 2,3-dihydroxybenzoic acid of the formula:

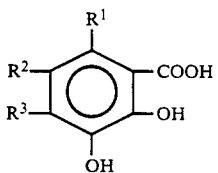

in which $R^1$, $R^2$, and $R^3$ are as herein defined, to the action of 2,3-dihydroxybenzoate-3,4-dioxygenase in a liquid medium lacking active decarboxylase and having a pH from 4 to 9, an ionic strength below about 1 molar, and a low concentration of metal cations and complex anions, to accumulate 2-hydroxy-3-carboxymuconic acid semialdehyde, and in sufficiently close temporal proximity to avoid substantial decarboxylation, reacting the 2-hydroxy-3-carboxymuconic acid semialdehyde thus formed with a source of ammonia or a primary amine.

2. The process according to claim 1 wherein said 2,3-dihydroxybenzoic acid is subjected to the action of a 2,3-dihydroxybenzoate-3,4-dioxygenase in the presence of ammonia.

3. The process according to claim 1 said 2,3-dihydroxybenzoate-3,4-dioxygenase has been expressed by a recombinant vector which does not express active decarboxylase for 2-hydroxy-3-carboxymuconic acid semialdehyde.

4. The process according to claim 1 wherein said 2,3-dihydroxybenzoate-3,4-dioxygenase is unbound in the form of a whole-cell or cell-free preparation.

5. The process according to claim 1 wherein said 2,3-dihydroxybenzoate-3,4-dioxygenase is immobilized on a support.

6. The process according to claim 1 wherein $R^1$ and $R^3$ are hydrogen and $R^2$ is hydrogen or alkyl of 1 to 6 carbon atoms, unsubstituted or substituted with halo or alkoxy of 1 to 6 carbon atoms.

7. The process according to claim 6 wherein said 2,3-dihydroxybenzoic acid is selected from the group consisting of (i) a 2,3-dihydroxybenzoic acid which is 2,3-dihydroxybenzoic acid, 2,3-dihydroxy-5-methylbenzoic acid, 2,3-dihydroxy-5-ethylbenzoic acid, 2,3-dihydroxy-5-bromomethylbenzoic acid, 2,3-dihydroxy-5-chloromethylbenzoic acid, 2,3-dihydroxy-5-dibromomethylbenzoic acid, 2,3-dihydroxy-5-dichloromethylbenzoic acid, 3,4-dihydroxy-2-carboxynaphthalene, 2,3-dihydroxy-5-methoxymethylbenzoic acid, 2,3-dihydroxy-5-ethoxymethylbenzoic acid, 2,3-dihydroxy-5-propoxymethylbenzoic acid, or 2,3-dihydroxy-5-isopropoxymethylbenzoic acid, and (ii) biological precursors therefor.

8. The process according to claim 7 wherein said 2,3-dihydroxybenzoic acid is 2,3-dihydroxybenzoic acid.

9. The process according to claim 7 wherein said 2,3-dihydroxybenzoic acid is 2,3-dihydroxy-5-ethylbenzoic acid.

10. The process according to claim 1 wherein the temperature is maintained below about 50° C.

11. The process according to claim 1 wherein the concentration of complex anions is below about 100 mM.

12. The process according to claim 11 wherein the concentration of phosphate anions is below about 100 mM.

13. The process according to claim 1 wherein said 2,3-dihydroxybenzoic acid is generated from a benzoic acid of the formula:

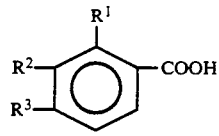

in which $R^1$, $R^2$, and $R^3$ are as herein defined, is subjected to the action of a 2,3-oxygenase under enzymatically reactive conditions.

* * * * *